US009955897B2

United States Patent
Senegas et al.

(10) Patent No.: US 9,955,897 B2
(45) Date of Patent: May 1, 2018

(54) PREDICTION, SCORING, AND CLASSIFICATION OF MAGNETIC RESONANCE CONTRAST USING CONTRAST SIGNAL SCORING EQUATION

(71) Applicant: KONINKLIJKE PHILIPS N.V., Eindhoven (NL)

(72) Inventors: Julien Senegas, Hamburg (DE); Peter Koken, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 337 days.

(21) Appl. No.: 14/414,552

(22) PCT Filed: Jul. 10, 2013

(86) PCT No.: PCT/IB2013/055678
§ 371 (c)(1),
(2) Date: Jan. 13, 2015

(87) PCT Pub. No.: WO2014/013390
PCT Pub. Date: Jan. 23, 2014

(65) Prior Publication Data
US 2015/0216440 A1    Aug. 6, 2015

Related U.S. Application Data

(60) Provisional application No. 61/671,822, filed on Jul. 16, 2012.

(51) Int. Cl.
*A61B 5/055*    (2006.01)
*G01R 33/54*    (2006.01)
(Continued)

(52) U.S. Cl.
CPC ............ *A61B 5/055* (2013.01); *A61B 5/7225* (2013.01); *A61B 5/7264* (2013.01); *A61B 5/742* (2013.01);
(Continued)

(58) Field of Classification Search
None
See application file for complete search history.

(56) References Cited

U.S. PATENT DOCUMENTS 5,754,697 A    5/1998    Fu et al.
6,219,571 B1    4/2001    Hargreaves
(Continued)

OTHER PUBLICATIONS

Haacke et al. "Contrast Mechanism in MRI and Contrast Maximization," Magnetic Resonance Imaging—Physical Principles and Sequence Design, 1999, pp. 352-363.*
(Continued)

*Primary Examiner* — Tse Chen
*Assistant Examiner* — Nate S Sunwoo (57) ABSTRACT

A magnetic resonance imaging sequence is defined by an imaging protocol and parameter values for a set of parameters of the imaging protocol. A contrast signal score is computed for the magnetic resonance imaging sequence respective to a contrast type to be scored using a scoring equation. A contrast type is determined for the magnetic resonance imaging sequence based on the computed contrast signal score. In one approach, the computing is repeated for a plurality of different contrast types to be scored, and the determining is based on the computed contrast signal scores.

16 Claims, 5 Drawing Sheets

(51) Int. Cl.
  *G06F 19/00* (2018.01)
  *A61B 5/00* (2006.01)
  *G01R 33/56* (2006.01)

(52) U.S. Cl.
  CPC ............ *A61B 5/746* (2013.01); *A61B 5/7475* (2013.01); *G01R 33/543* (2013.01); *G01R 33/5601* (2013.01); *G06F 19/3406* (2013.01); *A61B 2560/0475* (2013.01); *A61B 2576/00* (2013.01); *G01R 33/5602* (2013.01)

(56) References Cited

U.S. PATENT DOCUMENTS

| | | | |
|---|---|---|---|
| 6,687,527 B1* | 2/2004 | Wu | G01R 33/546 324/318 |
| 6,888,350 B2 | 5/2005 | Deimling | |
| 7,822,242 B2 | 10/2010 | Kobayashi et al. | |
| 2003/0092981 A1 | 5/2003 | Deimling | |
| 2006/0279282 A1 | 12/2006 | Van Den Brink | |
| 2008/0219527 A1 | 9/2008 | Lavi et al. | |
| 2009/0207968 A1 | 8/2009 | Grass | |
| 2009/0267599 A1 | 10/2009 | Warntjes | |
| 2009/0278536 A1 | 11/2009 | Winkelmann et al. | |

OTHER PUBLICATIONS

Preston, "Magnetic Resonance Imaging (MRI) of the Brain and Spine: Basics," Nov. 30, 2006, <http://casemed.case.edu/clerkships/neurology/Web%20Neurorad/MRI%20Basics.htm>.*
Trick, "Unconstrained Optimization: Functions of Several Variables," Carnegie Mellon University, Aug. 24, 1998, pp. 37-42.*
Hess et al., "Exploring the Brain: How Are Brain Images Made with MRI?," Apr. 5, 2012, University of California, San Francisco, <https://radiology.ucsf.edu/blog/neuroradiology/exploringthebrainhowarebrainimagesmadewithmri>.*
Haacke, E.M. et al "Contrast Mechanisms in MRI and Contrast Maximization" Magnetic Resonance Imaging—Physical Principles and Sequene Design, 1999. pp. 352-363.
Van Der Meulen, P. et al "Fast Field Echo Imaging: An Overview and Contrast Calculations", Magnetic Resonance Imaging, vol. 6, 1988, pp. 355-368.
Busse, Reed F. et al "Interactive Fast Spin-Echo Imaging", Magnetic Resonance in Medicine, vol. 44, 2000, pp. 339-348.
Haacke et al "Magnetic Resonance Imaging, Physical Principles and Sequence Design" John Wiley & Sons (1999) p. 352-366.
Busse et al "Interactive Fast Spin-Echo Imaging" Magnetic Resonance in Medicine, vol. 44, p. 339-348 (2000).
Van Der Meulen et al "Fast Field Echo Imaging an Overview and Contrast Calculations" Magnetic Resonance Imaging, vol. 6,p. 355-368 (1988).

* cited by examiner

PREDICTION, SCORING, AND CLASSIFICATION OF MAGNETIC RESONANCE CONTRAST USING CONTRAST SIGNAL SCORING EQUATION

CROSS-REFERENCE TO PRIOR APPLICATIONS

This application is the U.S. National Phase application under 35 U.S.C. § 371 of International Application No. PCT/IB2013/055678, filed on Jul. 10, 2013, which claims the benefit of U.S. Provisional Patent Application No. 61/671,822, filed on Jul. 16, 2012. These applications are hereby incorporated by reference herein.

DESCRIPTION

The following relates to the magnetic resonance arts, magnetic resonance imaging arts, medical imaging arts, imaging session planning arts, image archiving arts, imaging protocol design arts, and so forth.

In magnetic resonance (MR) imaging, a radiologist or other operator selects an imaging protocol which defines the structure of the sequence, e.g. the number and arrangement of radio frequency (RF) and magnetic field gradient pulses, readout operations, and so forth. The imaging protocol is usually designed to provide a particular type of contrast, e.g. T1 contrast, T2 contrast, T2* contrast, diffusion weighted contrast, or so forth. In the case of T1, T2, or T2* contrast, the imaging provides contrast for differences in the T1, T2, or T2* (resp.) relaxation time of the tissue or other substance being imaged. Protocol parameters such as the time-to-echo (TE), sequence repetition time (TR), excitation flip angle (FA), and so forth affect the strength of T1, T2, or T2* contrast. In other types of contrast, the protocol includes preparatory or magnetic resonance-manipulative RF pulses and/or magnetic field gradients that are applied to generate the desired contrast. For example, in diffusion weighted imaging the protocol is designed to provide contrast based on local molecular diffusion characteristics.

A given protocol has a set of parameters (e.g., TE, TR, FA, parameters defining a preparatory pulse, or so forth). The parameters may have different representations in different protocols. For example, in a multi-slice imaging protocol which acquires a set of slices in response to successive RF excitations, the number of slices may be specified, and the TR value then calculated to be as small as possible (e.g., to facilitate rapid imaging). In this case, adjusting the number of slices impacts the TR value. In such a case, the radiologist may increase or decrease the number of slices in order to adjust image resolution transverse to the slices, or to increase the total imaging volume. In doing so, the radiologist may fail to appreciate that the value of the TR parameter is simultaneously being adjusted.

In clinical practice, the radiologist typically has available a library of protocols tailored for various contrast types and for various tissue types. Each protocol usually includes a set of default parameter values, e.g. a default TE, TR, FA, et cetera. The radiologist is not limited to these default parameter values, however, but instead has the option to adjust some or all of the parameter values to optimize the protocol for a particular patient, for a particular imaging situation, or to accommodate personal preferences of the radiologist or of the physician ordering the MR study.

Adjusting the protocol parameters requires expert training, and the MR operator is typically a trained radiologist or otherwise qualified person. The radiologist may reference recommendations from MR literature, a published user guide for the MR scanner, Internet-based radiology user forums, or so forth. In practice, however, the radiologist has a scheduled time window in which to perform an imaging session, and usually relies upon personal expertise in making protocol parameter adjustments. It can happen that subtle changes in the parameters have an undesired influence on the resulting image contrast. For example, as already noted, adjusting the slice number in a multi-slice imaging protocol can have a latent impact on the TR value, which in turn can impact contrast.

Similar problems can arise if the default protocol is mislabeled in the protocols library. This can occur due to error, or because different medical professionals may have different opinions as to what constitutes a given contrast type. In practice, a given MR image may exhibit a blend of different contrast types, e.g. predominantly T2 contrast but with some T1 contrast as well, and different persons may have different views as to whether a given image exhibits "adequate" T2 contrast.

Images with the wrong contrast, or with severely degraded contrast or with a blend of contrasts, can be of little clinical value. The MR images may be misinterpreted, or the entire MR study may need to be redone, which is inconvenient for the patient, costly, and can lead to delay in medical treatment.

These problems can extend into post-acquisition image processing or analysis. For example, a Picture Archiving and Communications Service (PACS) is typically employed to archive medical images, for example stored in accord with the Digital Imaging and COmmunication in Medicine (DICOM) standard. A patient's MR images may be compared with images stored in a PACS in order to identify similar cases. While such comparisons can be medically useful, the validity of the comparison can be compromised if the image contrast is different in the patient and archive images. The likelihood of such a difference is increased if the PACS archives images from multiple medical facilities or different imaging laboratories that use different contrast standards.

The following contemplates improved apparatuses and methods that overcome the aforementioned limitations and others.

According to one aspect, a non-transitory storage medium stores instructions executable by an electronic data processing device to perform a method including: identifying a magnetic resonance imaging sequence defined by an imaging protocol and parameter values for a set of parameters of the imaging protocol; computing a contrast signal score for the magnetic resonance imaging sequence respective to a contrast type to be scored using a scoring equation; and determining a contrast type for the magnetic resonance imaging sequence based on the computed contrast signal score. In one approach, the computing is repeated for a plurality of different contrast types to be scored, and the determining is based on the computed contrast signal scores.

According to another aspect, an apparatus comprises a non-transitory storage medium as set forth in the immediately preceding paragraph and an electronic data processing device configured to read and execute the instructions stored on the non-transitory storage medium.

According to another aspect, a method comprises: identifying a magnetic resonance imaging sequence defined by an imaging protocol and parameter values for a set of parameters of the imaging protocol; computing a contrast signal score for the magnetic resonance imaging sequence respective to a contrast type to be scored using a scoring equation; and determining a contrast type for the magnetic resonance imaging sequence based on the computed contrast signal score. In one approach, the computing is repeated for a plurality of different contrast types to be scored. The computing and determining are performed by an electronic data processing device.

One advantage resides in providing real-time feedback on the impact of protocol parameter adjustments on the expected image contrast.

Another advantage resides in providing a principled approach for labeling MR imaging protocols and archived MR images as pertaining to image contrast type.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

Figure 1:
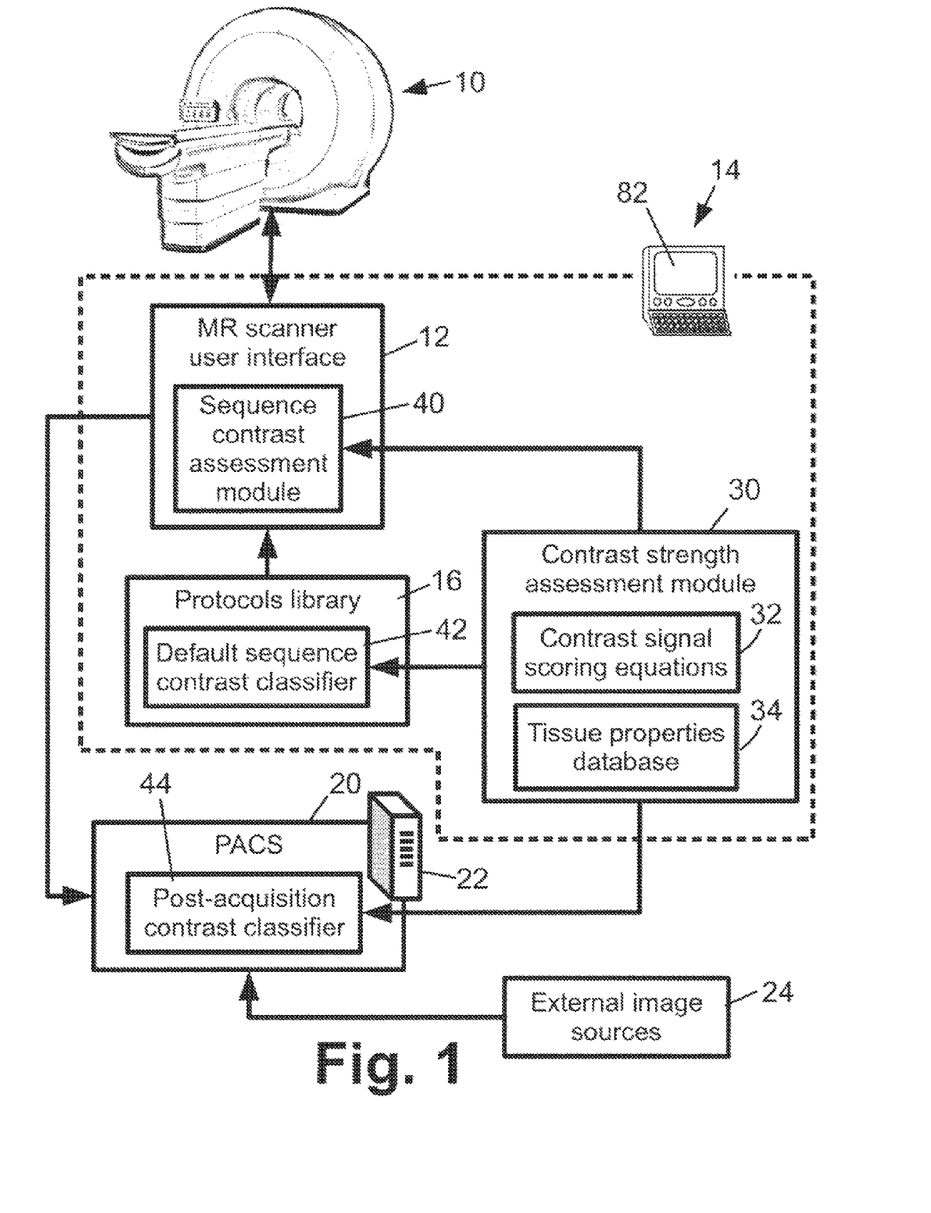
FIG. 1 diagrammatically shows a system for acquiring and archiving magnetic resonance (MR) images.

With reference to FIG. 1, a magnetic resonance (MR) scanner 10 is operated by a radiologist or other user via an MR scanner user interface 12, for example suitably embodied by an illustrative computer 14 or other electronic data processing device with user-interfacing hardware (e.g., an LCD display or other-type display, a keyboard, mouse, and/or other user input device(s), or so forth). The MR scanner 10 may be any commercial MR scanner, such as an Achieva™, Ingenia™, Intera™, or Panorama™ MR scanner available from Koninklijke Philips Electronics N.V., Eindhoven, The Netherlands, or a commercial MR scanner from another vendor. Alternatively, the MR scanner 10 can be a custom-built or modified MR scanner.

To perform an image acquisition, a patient or other human subject is loaded into the MR scanner 10. Various preparatory operations may be performed, such as immobilizing the patient, loading local MR coils, or so forth. While imaging of a human subject is described, it is also contemplated to image a veterinary subject (e.g., dog or cat), or a mummy, cadaver, or other deceased human or animal subject, or an inanimate object.

The radiologist or other user selects an imaging protocol from a protocols library 16. The protocol is selected based on considerations such as the type of image contrast that is desired (e.g., T1 contrast, T2 contrast, T2* contrast, diffusion weighted contrast, et cetera), the type of tissue to be imaged (e.g., brain imaging, cardiac imaging, et cetera), the size and dimensions of the imaging volume of interest, and so forth. The user also selects parameter values for the parameters of the selected protocol. The protocol parameters may, for example, include one or more of the following: time-to-echo (TE), repetition time (TR), excitation flip angle (FA), parameters defining a preparatory radio frequency (RF) or magnetic field gradient pulse or set of such preparatory pulses, or so forth. In some embodiments the protocol parameters may also include image reconstruction parameters such as reconstruction algorithm, resolution, filtering parameters, or so forth.

As used herein, the imaging protocol with a particular set of parameter values is referred to herein as an imaging sequence. The protocols library 16 may store default parameter values for the selected protocol, and the selected protocol with the default parameter values is referred to herein as the default imaging sequence. The user may choose to perform the imaging using the default parameter values, or may choose to adjust the value of one or more parameters. Moreover, while typically the selected protocol is provided with default parameters in the library 16, it is also contemplated for the protocol to have no default parameter values, in which case the user will select all parameter values.

The imaging sequence is thus obtained, comprising the protocol with the parameter values chosen by the user (where "chosen" encompasses the possibility that the user chooses to retain the default parameter value). The user instructs the MR scanner 10 via the MR user interface 12 to perform the imaging sequence so as to cause the MR scanner 10 to execute the imaging sequence and acquire MR imaging data. In some embodiments the imaging protocol is considered to include the image reconstruction process, in which case execution of the imaging sequence also includes reconstructing the MR imaging data in accordance with the selected reconstruction parameter values in order to generate one or more reconstructed MR images. (In other contemplated embodiments, the imaging protocol is not deemed to include the reconstruction process, in which case MR imaging data is acquired in accord with the imaging sequence and the MR imaging data is reconstructed to generate one or more reconstructed MR images but in these embodiments the reconstruction process is not in accord with parameters of the imaging protocol).

The one or more reconstructed images can be variously used. For example, the images may be reviewed on the display of the computer 14, printed using a suitable graphical marking engine, and/or stored in a Picture Archiving and Communications Service (PACS) 20, for example stored in accord with the Digital Imaging and COmmunication in Medicine (DICOM) standard. The PACS 20 is suitably embodied by a server 22 or other electronic data processing device. In some embodiments (not illustrated), the PACS may be embodied by the same computer that embodies the MR scanner user interface. Moreover, the PACS 20 may receive and archive images acquired from other (i.e., "external") image sources 24, e.g. other MR laboratories or other hospitals.

With continuing reference to FIG. 1, the system further includes a contrast strength assessment module 30 which is configured to analytically compute a contrast signal score for the MR imaging sequence. The contrast strength assessment module 30 suitably computes the contrast signal score for the MR imaging sequence respective to a contrast type to be scored (e.g., T1 weighted contrast, T2 weighted contrast, T2* weighted contrast, diffusion weighted contrast, et cetera) using a scoring equation. The computation is based on MR physics, not on empirical measurements of the subject. In its general form, the image contrast is due to a change in the measured MR signal due to a (usually relatively small) change in a characteristic that varies within the region being imaged. In the case of T1 weighted imaging, the contrast is due to relatively small differences in the T1 relaxation time of different tissues (e.g., water versus fat versus bone, et cetera). Similarly, T2 weighted imaging shows contrast for differences in the T2 relaxation time of different tissue types. In the case of diffusion weighted imaging, the contrast is due to relatively small differences in MR signal due to local variations in molecular diffusion. In view of this, the scoring equation suitably includes a partial derivative $$\frac{\partial S(p)}{\partial p}$$

where p denotes an expected value for the characteristic producing the contrast to be scored and S(p) denotes the signal generated by the magnetic resonance imaging sequence for a substance having the expected value p for the characteristic producing the contrast to be scored. Said another way, S(p) denotes the signal generated by the magnetic resonance imaging sequence as a function of characteristic p whose variation gives rise to the contrast type to be scored. In the case of scoring T1 weighted contrast, for example, the characteristic p whose variation gives rise to the T1 contrast is the T1 relaxation time of the various imaged tissues. In the case of scoring T2 weighed contrast, the characteristic p whose variation gives rise to the T2 contrast is the T2 relaxation time of the various imaged tissues. The characteristic p whose variation gives rise to the contrast type to be scored does not have to be a tissue characteristic. For example, in the case of magnetic resonance angiography (MRA) the characteristic p may be blood velocity (for time-of-flight MRA), or exogenous contrast agent concentration (when using an administered exogenous vascular contrast agent such as a gadolinium-based magnetic contrast agent). Since the signal S(p) is expected to vary relatively smoothly and relatively slowly with changes in the value of the characteristic p, the precise choice of the "expected value" of the characteristic p is usually not critical. For example, in the case of computing a contrast signal score for T1 weighted contrast for brain protocols, the expected value p can be the T1 relaxation time for grey water or for white matter or for some average or "composite" tissue (e.g. an average of the relaxation times for grey and white matter).

The scoring equation can be approximate, for example using a difference approximation for the partial derivative $$\frac{\partial S(p)}{\partial p}.$$

In some contemplated embodiments a difference approximation is chosen in which a difference Δp corresponds to an expected actual difference in the subject. For example, in the case of brain imaging where the image is intended to distinguish between grey brain matter and white brain matter, a suitable difference approximation is $$\frac{\partial S(p)}{\partial p} \sim \left| \frac{S(p_{grey}) - S(p_{white})}{p_{grey} - p_{white}} \right|.$$

As will be observed in this illustrative approximation, it is contemplated for the partial derivative $$\frac{\partial S(p)}{\partial p}$$

to include an absolute value operation to ensure a positive contrast signal score. In the case of T1 weighting for brain imaging, this illustrative difference approximation becomes $$\frac{\partial S(p)}{\partial p} \sim \left| \frac{S(T_{1,grey}) - S(T_{1,white})}{T_{1,grey} - T_{1,white}} \right|$$

where $T_{1,grey}$ is the T1 relaxation time of grey brain matter and $T_{1,white}$ is the T1 relaxation time of white brain matter. As another illustrative example, the scoring equation can be:

$$\text{score}(p) = \frac{\partial S(p)}{\partial p} \cdot \frac{p}{S(p)} \approx \frac{\frac{S(p+0.5\Delta p) - S(p-0.5\Delta p)}{S(p)}}{\frac{\Delta p}{p}}$$

where Δp=δ·p for some small δ and again an absolute value operation can optionally be added to ensure positive contrast signal scores.

With continuing reference to FIG. 1, the contrast strength assessment module 30 includes or has access to a database containing the contrast signal scoring equations 32. The contrast strength assessment module 30 also includes or has access to a tissue properties database 34 which stores values for at least those tissue properties used in the scoring equations 32. These values typically include representative T1, T2, and T2* relaxation times for tissue expected to be considered during the imaging. These values may be dependent on the strength of the main field of the MR system (e.g. 1 T, 1.5 T, 3 T, or 7 T) or of other parameters, such as the room temperature. If the contrast strength assessment module 30 is configured to score diffusion weighted contrast, then the tissue properties database 34 suitably includes representative molecular diffusion parameters. The stored tissue properties may include other tissue property values needed to compute the MR signal S(p) based on MR physics, e.g. magnetic permeability values of the tissue or so forth. It should also be noted that in the case of inanimate object imaging applications, the tissue properties database may be replaced by an analogous substance properties database.

With continuing reference to FIG. 1, the contrast strength assessment module 30 can be utilized in various aspects of the MR imaging process. For example, the illustrative MR scanner user interface 12 includes a sequence contrast assessment module 40 which uses the contrast strength assessment module 30 to assess the strength of various contrast types for the imaging sequence so as to identify the dominant contrast type provided by the sequence. Since the contrast strength assessment module 30 computes the contrast signal score analytically, it is fast and so the sequence contrast assessment module 40 can be invoked immediately after each adjustment of any protocol parameter value. In this way, the user can be informed immediately if the parameter value adjustment would have the effect of changing the dominant contrast type of the imaging sequence.

As another illustrative application, the protocols library 16 includes a default sequence contrast classifier 42. Typically, the protocols stored in the protocols library 16 are designed by experts in magnetic resonance imaging to provide a desired contrast type, and toward this end typically the protocol will include a set of default parameters (thus defining a default imaging sequence) that the expert considers to provide the desired contrast. However, there is some subjectivity in assessment of the contrast type of a sequence since the overall contrast is typically a blend of various contrast types. The sequence contrast classifier 42 invokes the contrast strength assessment module 30 to apply the contrast signal scoring equations 32 so as to determine which contrast type is dominant. By applying the same set of equations 32 to all default sequences of the protocol library 16 a more uniform standard is provided for labeling the contrast type of the default sequences.

As another illustrative application, the PACS 20 includes a post-acquisition contrast classifier 44 that labels images by contrast type. If the PACS 20 employs a DICOM format or other storage format that includes image metadata, then the images may be (and in the case of the DICOM format usually are) labeled with contrast type, along with metadata identifying the imaging protocol and the protocol parameter values used in the image acquisition. However, the contrast type label is usually assigned manually, by the radiologist or other user based on personal expertise. Again, the subjectivity of defining the dominant contrast type means that this manual labeling may have some undesirable variance. Such variance can be problematic if medical personnel look to the PACS 20 as a reference images database since differences in contrast type can complicate or invalidate image comparisons. Accordingly, the post-acquisition contrast classifier 44 retrieves the image metadata identifying the protocol and protocol parameters used in the acquisition and invokes the contrast strength assessment module 30 to apply the appropriate contrast signal scoring equation 32 to determine the dominant contrast type, and the post-acquisition contrast classifier 44 then labels the image with that contrast type. The automatically generated contrast type label can be stored as an image metadata element that is separate from the manually applied contrast type label, or the automatically generated contrast type label can replace the manually applied contrast type label in the image metadata.

Figure 2:
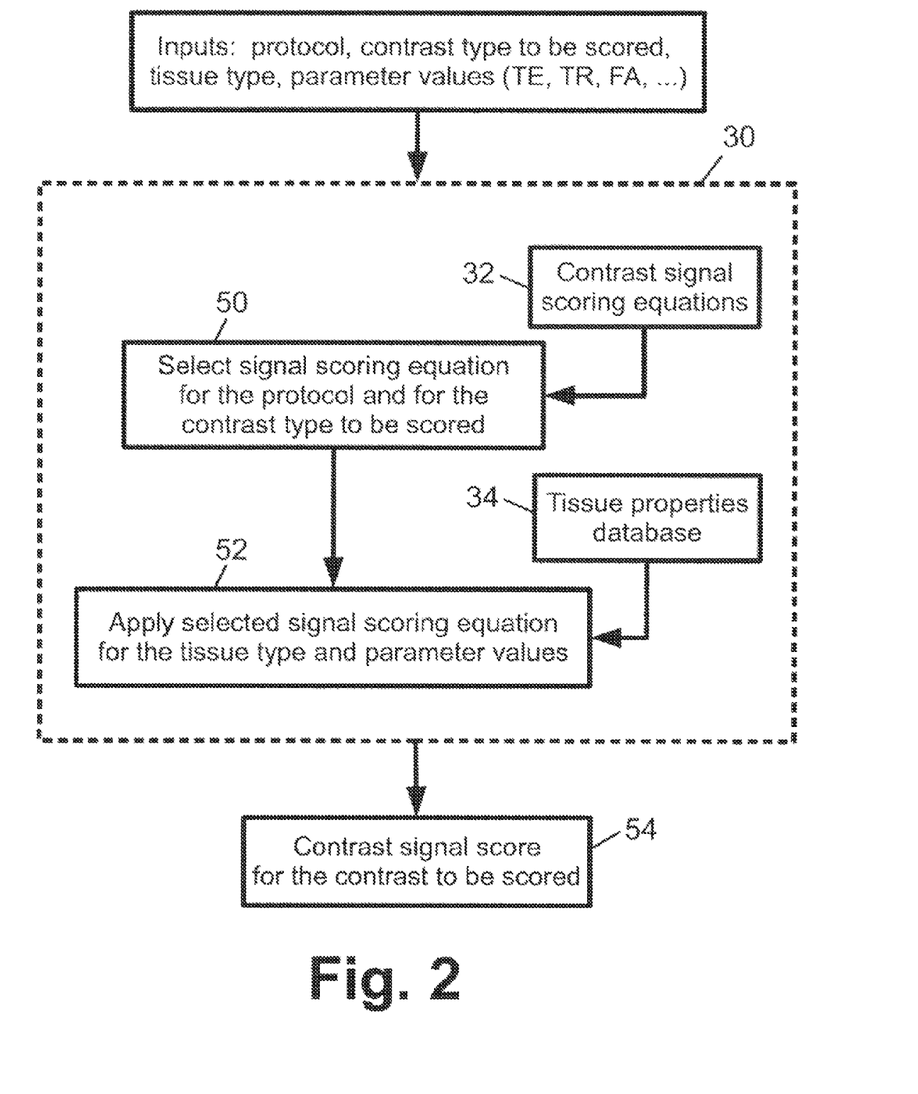
FIG. 2 diagrammatically shows the contrast strength assessment module of the system of FIG. 1.

With reference to FIG. 2, an illustrative example of the contrast strength assessment module 30 is shown. The module 30 receives as input from the MR scanner user interface 12 the imaging sequence (defined by the protocol selected by the user and the current protocol parameter values), the tissue type (optional; in some embodiments the tissue type is an a priori known value), and the contrast type to be scored. The imaging sequence defined by the protocol and protocol parameters may, for example, be an inversion recovery (IR) sequence, a spin echo (SE) sequence, a fast field echo (FFE) sequence, or so forth. The imaging sequence may be configured to acquire two-dimensional data (e.g., a slice), three-dimensional data, or a set of multiple (sequential) two-dimensional (M2D) slices. The imaging sequence may also employ a fast acquisition mode, e.g. echo planar imaging (EPI), turbo spin echo (TSE) imaging, turbo field echo (TFE) imaging, gradient and spin echo (GRASE) imaging, various combinations thereof (e.g., TFEEPI), or so forth. In an operation 50, the module 30 selects the signal scoring equation appropriate for the protocol and for the contrast type to be scored. In an operation 52 the selected signal scoring equation is applied for the tissue type and parameter values to generate a contrast signal score 54 for the contrast to be scored.

The signal equation describes the MR signal intensity as a function of the protocol parameters (such as echo time TE, repetition time TR, flip angle FA, and so forth) and known contrast parameters reflecting tissue properties (such as T1 relaxation and T2 relaxation rates). As already noted, the signal scoring equation suitably incorporates the partial derivative $$\frac{\partial S(p)}{\partial p}$$

of the MR signal respective to the expected relaxation time p for the contrast type to be score (in the case of T1, T2, or T2* weighted contrast) or other characteristic p producing the contrast to be scored (e.g., in the case of diffusion weighted contrast). Some suitable analytical expressions of the signal equation S(p) for various imaging sequences can be found in the literature, for example: van der Meulen et al, MRI; 6:355-368 (1988); Haacke et al. Magnetic Resonance Imaging. Physical principles and sequence design (1999); Busse et al, MRM, 44:339-348 (2000); Bernstein et al. Handbook of MRI Pulse Sequences (2004); and Liang and Lauterbur, Principles of Magnetic Resonance Imaging, A Signal Processing Perspective (2000).

Figure 3:
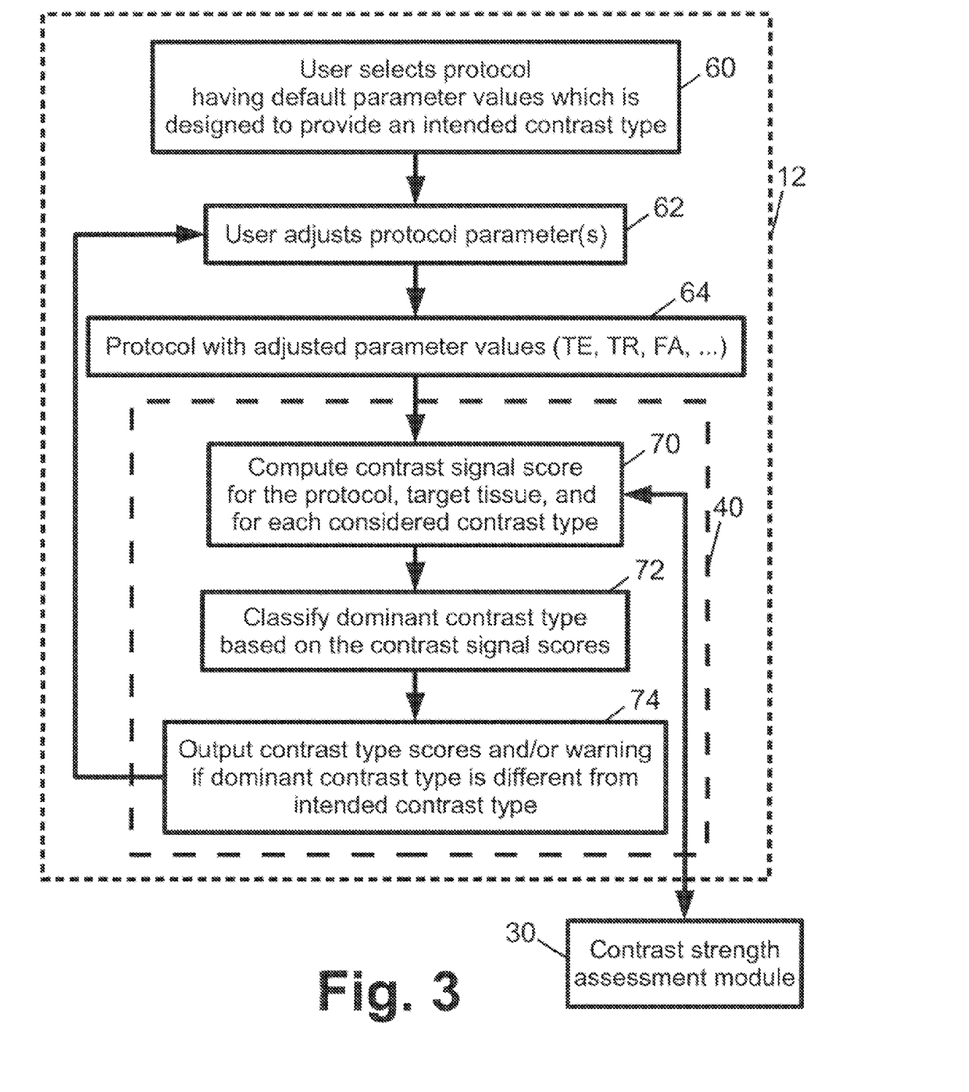
FIG. 3 diagrammatically shows the sequence contrast assessment module of the MRT scanner/user interface of the system of FIG. 1.

With reference to FIG. 3, an illustrative embodiment of the sequence contrast assessment module 40 utilized by the MR scanner user interface 12 is described. In an operation 60 the user selects the protocol having default parameter values (i.e. a default imaging sequence) designed to provide an intended contrast type. In an operation 62 the user adjusts one or more of the parameter values to generate a protocol with adjusted parameter values 64. The operations 60, 62 are suitably performed using the MR scanner user interface 12; however, some of the parameter value adjustments may be done other than explicitly. For example, in a multi-slice imaging technique having a minimized TR, adjustment of the number of slices indirectly causes adjustment of TR.

Each time an adjusted set of parameter values 64 is generated, the sequence contrast assessment module 40 is invoked. In an operation 70, the module 40 computes, for each considered contrast type, the contrast signal score for the imaging sequence defined by the protocol and the adjusted protocol parameter values 64. For example, consider an illustrative example in which the intended contrast type of the default sequence chosen in operation 60 is T2 weighted contrast. The operation 70 suitably computes a contrast signal score for each of T1 weighting, T2 weighting and (optionally) T2* weighting. The operation 70 computes the contrast signal scores by invoking the contrast strength assessment module 30 for each considered contrast type.

Thus, the output of the operation 70 is a set of contrast signal scores for a set of contemplated contrast types. An operation 72 then classifies the dominant contrast type based on the contrast signal scores. For example, an illustrative dominant contrast type classification system for considered contrast types of proton density weighted contrast (PDW), T1 weighted contrast (T1W), and T2 weighted contrast (T2W) employs a series of threshold numbers $a_1 < b_1 < c_1$ and $a_2 < b_2 < c_2$. The contrast signal scores are suitably represented as score(T1) for T1W and score(T2) for T2W where T1 and T2 are the expected T1 and T2 relaxation times, respectively. (Again, T1 and T2 are representative values, e.g. grey matter T1, or white matter T1, or an average of grey matter and white matter T1). In this context, the following dominant contrast type classes can be defined for a spin echo (SE) sequence:

| Dominant contrast type classification rules | | | | |
|---|---|---|---|---|
| score(T1) < $a_1$ | and | score(T2) < $a_2$ | → | PDW |
| score(T1) < $a_1$ | and | $a_2$ < score(T2) < $b_2$ | → | Weak T2W |
| score(T1) < $a_1$ | and | $b_2$ < score(T2) < $c_2$ | → | T2W |
| score(T1) < $a_1$ | and | score(T2) > $c_2$ | → | Strong T2W |
| $a_1$ < score(T1) < $b_1$ | and | score(T2) < $a_2$ | → | Weak T1W |
| $b_1$ < score(T1) < $c_1$ | and | score(T2) < $a_2$ | → | T1W |
| score(T1) > $c_1$ | and | score(T2) < $a_2$ | → | Strong T1W |
| $a_1$ < score(T1) < $b_1$ | and | $a_2$ < score(T2) < $b_2$ | → | Weak T1W/ Weak T2W |
| $b_1$ < score(T1) < $c_1$ | and | $a_2$ < score(T2) < $b_2$ | → | T1W/Weak T2W |
| score(T1) > $c_1$ | and | $a_2$ < score(T2) < $b_2$ | → | Strong T1W/ Weak T2W |
| $a_1$ < score(T1) < $b_1$ | and | $b_2$ < score(T2) < $c_2$ | → | Weak T1W/T2W |
| $b_1$ < score(T1) < $c_1$ | and | $b_2$ < score(T2) < $c_2$ | → | T1W/T2W |
| score(T1) > $c_1$ | and | $b_2$ < score(T2) < $c_2$ | → | Strong T1W/T2W |
| $a_1$ < score(T1) < $b_1$ | and | score(T2) > $c_2$ | → | Weak T1W/ Strong T2W |
| $b_1$ < score(T1) < $c_1$ | and | score(T2) > $c_2$ | → | T1W/Strong T2W |
| score(T1) > $c_1$ | and | score(T2) > $c_2$ | → | Strong T1W/ Strong T2W |

In practice some contrast type classes listed above may be unachievable for the particular imaging protocol and the tissue being imaged.

Figure 4:
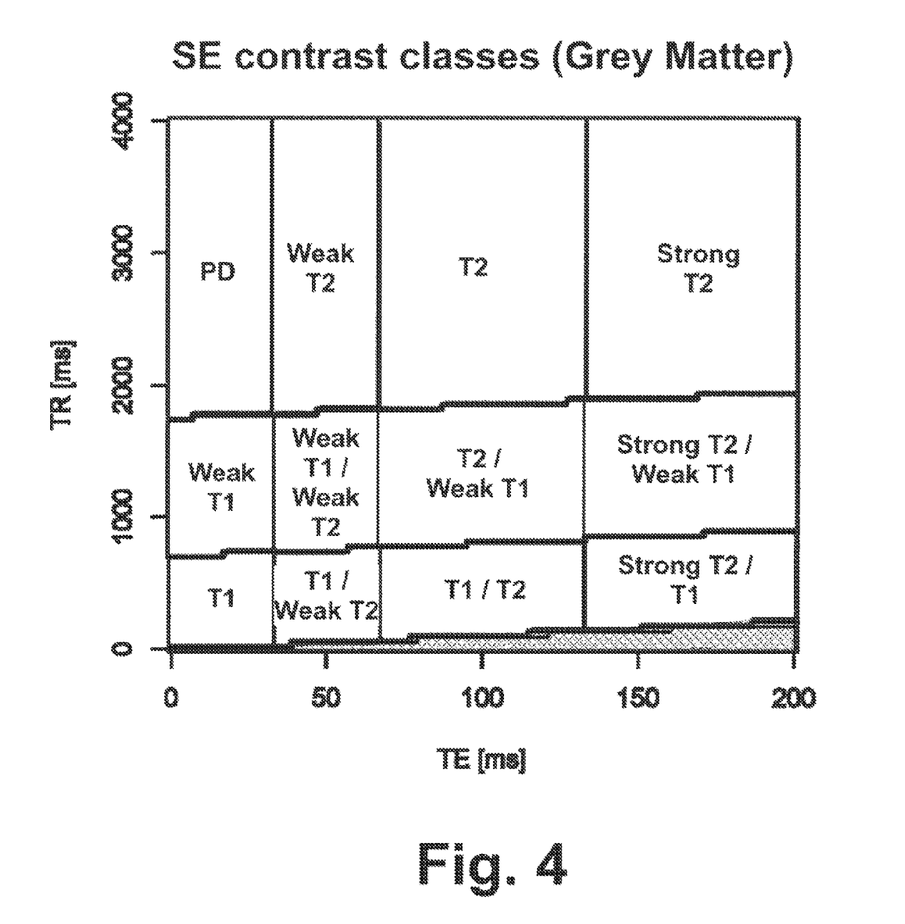
FIG. 4 diagrammatically shows an illustrative contrast type map for a TE-TR parameter space in the case of a spin echo (SE) sequence imaging grey matter in the brain.

With reference to FIG. 4, for example, contrast type classes achievable for a spin echo (SE) sequence imaging grey brain matter are shown. In the illustrative example of FIG. 2, the contrast class labels are mapped as function of echo time (TE) and repetition time (TR) in case of grey matter as reference tissue and 1.5 T as field strength. In this example, $a_1=a_2=0.33$, $b_1=b_2=0.67$, and $c_1=c_2=1.33$. In this example the blend of strong T1 and strong T2 contrast is not achievable. In the foregoing examples, the proton density weighting (PDW) is obtained when both T1W and T2W contrast are weak (i.e., score(T1)<$a_1$ and score(T2)<$a_2$). As seen in FIG. 4, PDW occurs for short TE and long TR— under these conditions the magnetic resonance signal has not appreciably decayed due to either T1 relaxation or T2 relaxation, and so differences in T1 or T2 relaxation time amongst different tissues does not provide contrast in the PDW image. The area grayed out in the lower right of FIG. 4 corresponds to the physically unrealizable condition of TE>TR.

Figure 5:
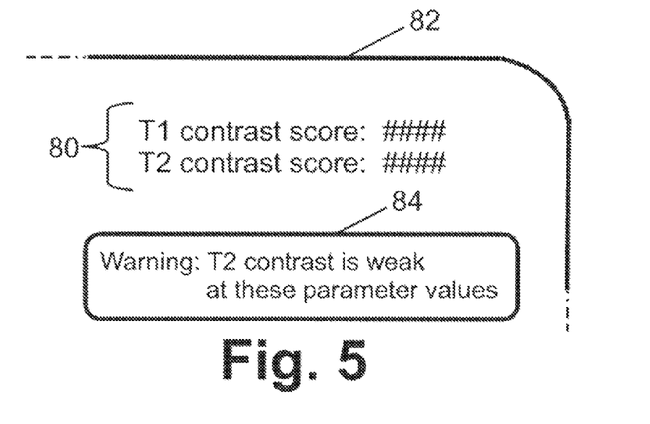
FIG. 5 diagrammatically shows a contemplated warning message displayed when the sequence contrast assessment module detects that an adjusted imaging sequence is likely to produce an image with the wrong contrast type.

With reference back to FIG. 3 and with further reference to FIG. 5, in an operation 74 performed by the sequence contrast assessment module 40, a suitable output is generated to inform the user about the contrast type scores. In some embodiments, the operation 74 displays a textual representation 80 of the contrast scores for the relevant contrast types on a display device 82 of the computer 14 (see also FIG. 1) implementing the MR scanner user interface 12. The absolute scores for the contrast types can be displayed, or alternative a percent change (or other relative change) of the contrast scores can be displayed respective to the scores for the default imaging sequence (or respective to another suitable scores baseline). Another option is to display a ratio of contrast scores, e.g. T2 contrast score/T1 contrast score. In addition to or instead of textual scores, a visual representation such as bars of lengths corresponding to the scores is also contemplated. Optionally, if the dominant contrast type output by the contrast type classification operation 72 is different from the intended contrast type of the default sequence selected in the operation 60, then a warning or some other type of remedial action is performed. As diagrammatically shown in FIG. 5, in one such optional warning approach the operation 74 displays a textual warning 84 on the display device 82. The textual warning 84 may include coloration (e.g. red background and/or red text) or animation (e.g. flashing) to increase likelihood that the user will notice the warning 84. Another possible remedial action, taken alone or in combination with the scores display 80 and the optional warning 84, is to "undo" (or refuse to accept) the protocol parameter adjustment that changed the predicted contrast type from the intended contrast type. It is also contemplated to provide the warning 84 without the scores display 80.

With continuing reference to FIG. 3 and with reference back to FIG. 1, a variant of the sequence contrast assessment module 40 is suitably employed in the default sequence contrast classifier 42 of the protocols library 16. In this case the input to the sequence contrast assessment module 40 is the default sequence defined by the protocol and its default parameter values, and the operation 74 is replaced by a protocol tagging operation that tags the protocol with the dominant contrast type class output by the operation 72. A variant of the sequence contrast assessment module 40 is also suitably employed in the post-acquisition contrast classifier 44 of the PACS 20. In this case the input to the sequence contrast assessment module 40 is the protocol and protocol parameter values tagged to the image stored in the PACS 20, and the operation 74 is replaced by an image tagging operation that tags the image with the dominant contrast type class output by the operation 72. In both the protocol tagging and image tagging operations, the tagging operation may be performed in combination with a warning delivered to the user if the original contrast type label of the protocol or image differs from that generated by the classification operation 72.

In addition to the foregoing illustrative application examples, the contrast strength assessment module 30 of FIG. 2 may find other applications. For example, the sequence contrast assessment module 40 provides a warning via the user interface 12 if the manually adjusted parameter values take the sequence away from the intended contrast type. However, in variant embodiments, more affirmative assistance is provided. For example, the partial derivatives of the scoring equation respective to the various parameters of the set of parameters of the imaging protocol can be evaluated (again using difference approximations) to determine which parameter is most affecting the contrast. For example, let $P_{max}$ denote the parameter having the most effect on contrast type p, as indicated by partial derivative $$\left| \frac{\partial \text{score}(p)}{\partial P_{max}} \right|$$

being larger than for any other protocol parameter. Then the direction of adjustment of the value of $P_{max}$ is positive if $$\frac{\partial \text{score}(p)}{\partial P_{max}} > 0$$

and is negative if $$\frac{\partial \text{score}(p)}{\partial P_{max}} < 0.$$

The amount of the adjustment of the value of $P_{max}$ can be estimated from the magnitude of the partial derivative $$\left|\frac{\partial \text{score}(p)}{\partial P_{max}}\right|.$$

With this information, a suggested parameter adjustment can be displayed based on the evaluated partial derivative.

As a further variant, the matrix of partial derivatives $$\frac{\partial \text{score}(p)}{\partial P}$$

for all protocol parameters P can be computed, and this matrix used in an optimization algorithm such as the Levenberg-Marquardt algorithm or a gradient descent method to optimize the values of the set of parameters to maximize the value of score(p) for the contrast type p. Optionally, one or more constraints can be placed on the optimization, e.g. maximize score(p) subject to the constraint that score(p) is larger than the contrast signal score for any other contrast type, and/or subject to the constraint TE<TR, or so forth. Thus, in this variant the parameter values are iteratively optimized to maximize the contrast type p to be scored (e.g., to maximize score(p)) where each iteration includes evaluating partial derivatives $$\frac{\partial \text{score}(p)}{\partial P}$$

of the scoring equation respective to parameters P of the set of parameters of the imaging protocol and adjusting one or more of the parameter values based on the evaluated partial derivatives. The user is then presented with the set of optimized parameter values.

While an optimization approach employing partial derivative of score (p) for the contrast type p is described, other approaches can be used to optimize the parameter values or to otherwise provide parameter value recommendations. For example, optimal parameter values satisfying certain conditions on the contrast type can be found by other methods that only use the score values (simplex algorithm, probabilistic methods, et cetera).

Figure 6:
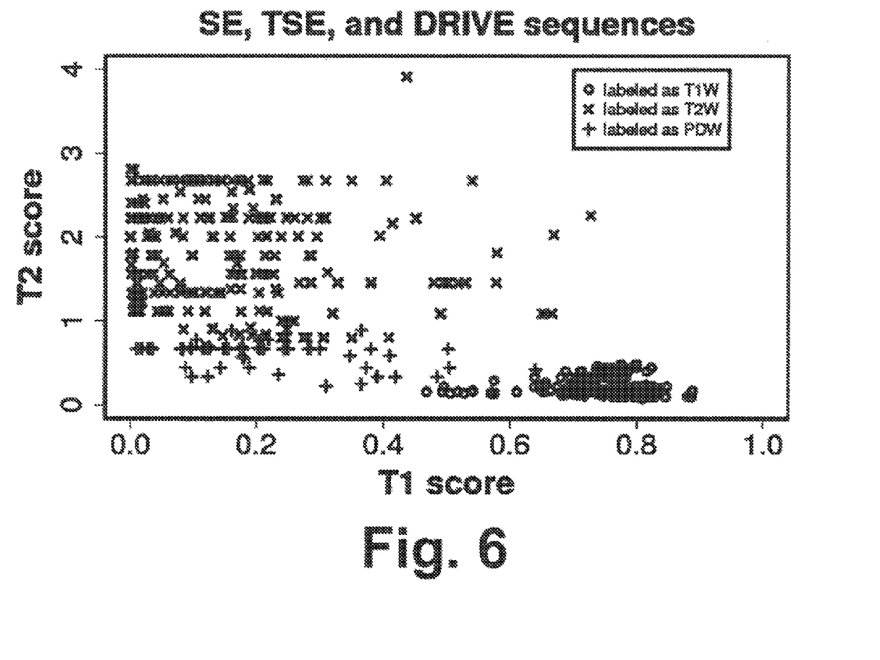
FIG. 6 plots the contrast type assessed using the approach disclosed herein for existing protocols, with each protocol marker being marked by a marker indicating the labeled contrast type of the protocol.

With reference to FIG. 6, the contrast type classification described herein was compared with contrast type classification labels assigned to various imaging sequences by human experts. FIG. 6 displays projections of different clinical spin-echo imaging sequences onto the space spanned by score(T1) and score(T2) computed as disclosed herein. A total of 1090 spin-echo protocols from 25 different MR scanners (13 with a main field of 1.5 T and 12 with a main field of 3 T), covering 18 different body parts, are displayed in FIG. 6. Each protocol was labeled as T1W (marked with circles in FIG. 6), T2W (marked with "x" in FIG. 6), or PDW (marked with "+" signs in FIG. 6), according to the protocol name given by the institution. Note that in some cases, this labeling may not be correct as the operator may have changed the default protocol parameters without modifying the protocol name. Nevertheless, it can be seen that these three different contrast classes are separated by the T1 and T2 score values computed herein. It can also be seen that some overlap is present, suggesting protocol settings that yield mixed contrast and may not be optimal with respect to the desired contrast.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A non-transitory storage medium storing instructions executable by an electronic data processing device to perform a method including:
   identifying a magnetic resonance imaging sequence defined by an imaging protocol, type of tissue to be imaged, and parameter values for a set of parameters of the imaging protocol;
   computing a contrast signal score for the magnetic resonance imaging sequence respective to a contrast type to be scored using a scoring equation;
   determining a contrast type for the magnetic resonance imaging sequence based on the computed contrast signal score;
   operating a magnetic resonance imaging (MRI) device using the magnetic resonance imaging sequence to generate a magnetic resonance image; and
   labeling the magnetic resonance image with the determined contrast type;
   wherein the scoring equation is:

$$\text{score}(p) = \frac{\partial S(p)}{\partial p} \cdot \frac{p}{S(p)}$$

where score (p) is the contrast signal score for the contrast type to be scored and S(p) denotes the signal generated by the magnetic resonance imaging sequence as a function of a characteristic p whose variation gives rise to the contrast type to be scored, the characteristic p including at least one of a T1 relaxation time of imaged tissues, a T2 relaxation time of images tissues, blood velocity, and exogenous contrast agent concentration.

2. The non-transitory storage medium of claim 1 wherein the computing is repeated for a plurality of different contrast types to be scored, and the determining is based on the computed contrast signal scores.

3. The non-transitory storage medium of claim 2 wherein the different contrast types to be scored include at least T1 weighted contrast and T2 weighted contrast.

4. The non-transitory storage medium of claim 1 wherein the computing includes approximating the partial derivative $$\frac{\partial S(p)}{\partial p}$$

of the scoring equation using a difference approximation.

5. A non-transitory storage medium storing instructions executable by an electronic data processing device to perform a method including:
   identifying a magnetic resonance imaging sequence defined by an imaging protocol having an intended contrast type, a type of tissue to be imaged, and parameter values for a set of parameters of the imaging protocol by monitoring user inputs to a magnetic resonance scanner user interface to detect user selection of the imaging protocol and user editing that changes one or more of the parameter values;

computing a contrast signal score for the magnetic resonance imaging sequence respective to a contrast type to be scored using a scoring equation;

determining a contrast type for the magnetic resonance imaging sequence based on the computed contrast signal score; and displaying a warning via the magnetic resonance user interface responsive to the determined contrast type for the magnetic resonance imaging sequence being different from the intended contrast type;

wherein the scoring equation includes the partial derivative:

$$\frac{\partial S(p)}{\partial p}$$

where S (p) denotes the signal generated by the magnetic resonance imaging sequence as a function of a characteristic p whose variation gives rise to the contrast type to be scored, the characteristic p including at least one of a T1 relaxation time of imaged tissues, a T2 relaxation time of images tissues, blood velocity, and exogenous contrast agent concentration.

6. The non-transitory storage medium of claim 5 wherein the method further comprises optimizing the scoring equation respective to at least one parameter of the set of parameters of the imaging protocol and displaying a suggested parameter adjustment based on the optimizing.

7. The non-transitory storage medium of claim 5 wherein the computing and determining is performed responsive to detection of user editing that changes one or more of the parameter values.

8. The non-transitory storage medium of claim 1 wherein the identifying includes detecting storing of the imaging protocol in a protocols library and the method further comprises labeling the stored imaging protocol with the determined contrast type.

9. The non-transitory storage medium of claim 1, wherein the identifying comprises reading the imaging protocol and the parameter values for the set of parameters of the imaging protocol from metadata stored with a stored magnetic resonance image.

10. The non-transitory storage medium of claim 9 wherein the method further comprises modifying the metadata stored with the magnetic resonance image to include the determined contrast type.

11. A method comprising:

identifying a magnetic resonance imaging sequence defined by an imaging protocol, type of tissue to be imaged, and parameter values for a set of parameters of the imaging protocol;

computing a contrast signal score for the magnetic resonance imaging sequence respective to a contrast type to be scored using a scoring equation;

determining a contrast type for the magnetic resonance imaging sequence based on the computed contrast signal score;

operating a magnetic resonance imaging (MRI) device using the magnetic resonance imaging sequence to generate a magnetic resonance image; and labeling the magnetic resonance image with the determined contrast type;

wherein at least the computing, the determining, and the labeling are performed by an electronic data processing device; and wherein the contrast type to be scored has an expected value p for a characteristic producing the contrast type to be scored and the scoring equation includes the partial derivative $\partial s(p)/\partial p$ where $S(p)$ denotes the signal generated by the magnetic resonance imaging sequence for a substance having the expected value p, the characteristic p including at least one of a T1 relaxation time of imaged tissues, a T2 relaxation time of images tissues, blood velocity, and exogenous contrast agent concentration.

12. The method of claim 11 wherein the computing is repeated for a plurality of different contrast types to be scored, and the determining is based on the computed contrast signal scores.

13. The method of claim 12 wherein the different contrast types to be scored include at least T1 weighted contrast and T2 weighted contrast.

14. The method of claim 11 wherein the identifying comprises detecting user editing of the parameter values via a magnetic resonance scanner user interface and the method further comprises:

comparing the determined contrast type for the magnetic resonance imaging sequence with an intended contrast type; and displaying a warning via the magnetic resonance user interface if the determined contrast type for the magnetic resonance imaging sequence is different from the intended contrast type.

15. The method of claim 11 further comprising:

optimizing the parameter values to maximize the contrast signal score wherein the optimizing includes evaluating partial derivatives of the scoring equation respective to parameters of the set of parameters of the imaging protocol.

16. The method of claim 11 wherein the identifying comprises reading the imaging protocol and the parameter values for the set of parameters of the imaging protocol from metadata stored with a magnetic resonance image and the method further comprises:

modifying the metadata stored with the magnetic resonance image to include the determined contrast type.

* * * * *